United States Patent [19]

Ishikawa et al.

[11] Patent Number: 5,116,838
[45] Date of Patent: May 26, 1992

[54] GUANIDINE DERIVATIVES AND FUNGICIDES FOR AGRICULTURE AND HORTICULTURE CONTAINING THE SAME

[75] Inventors: Hiromichi Ishikawa, Atsugi; Takashi Umeda, Sagamihara; Shinji Onoue, Atsugi; Kazuo Kajikawa, Atsugi; Toshihiro Shibata, Atsugi; Hiroshi Ohyama, Chigasaki, all of Japan

[73] Assignee: Hokko Chemical Industry Co., Ltd., Tokyo, Japan

[21] Appl. No.: 614,389

[22] Filed: Nov. 15, 1990

[30] Foreign Application Priority Data

Nov. 20, 1989 [JP] Japan .................................. 1-299655
Oct. 4, 1990 [JP] Japan .................................. 2-265230

[51] Int. Cl.$^5$ .................... A61K 31/155; C07C 279/16
[52] U.S. Cl. ...................................... 514/634; 564/237
[58] Field of Search ................. 564/237; 514/637, 634

[56] References Cited

FOREIGN PATENT DOCUMENTS 1170931  3/1962  Fed. Rep. of Germany .
  29742  6/1968  Japan .
   9846  4/1975  Japan .

Primary Examiner—Richard L. Raymond
Assistant Examiner—Shailendra Kumar
Attorney, Agent, or Firm—Abelman Frayne & Schwab

[57] ABSTRACT

There are disclosed novel 1,3-dibenzyl (or diphenethyl)-2-phenylguanidine derivatives. The guanidines possess high control effects on mildew, blight, powdery mildew and rust which are serious diseases of fruit trees, vegetables or cereals, and are useful as agricultural and horticultural fungicides.

2 Claims, No Drawings

GUANIDINE DERIVATIVES AND FUNGICIDES FOR AGRICULTURE AND HORTICULTURE CONTAINING THE SAME

BACKGROUND OF THE INVENTION

1. Field of the Invention

This invention relates to novel guanidine derivatives and fungicides for agriculture and horticulture containing said derivatives as an active ingredient.

2. Description of the Prior Art

Some of the literatures disclose guanidines. For example, Japanese Patent Publication No. 29742/1968 discloses a process for preparing substituted guanidines represented by the formula

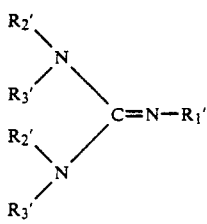

wherein $R'_1$ represents a substituted or unsubstituted aromatic hydrocarbon residue and $R'_2$ or $R'_3$ represents a hydrogen atom, a substituted or unsubstituted aromatic hydrocarbon residue.

There are also disclosed in Japanese Patent Publication No. 9846/1975 guanidines represented by the formula

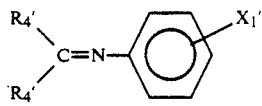

wherein $X'_1$ represents a hydrogen atom or a chlorine atom and $R'_4$ represents a benzylamino group or the like which have insecticidal and acaricidal activities as well as plant disease controlling activity.

Although the known guanidines have some fungicidal activities for agriculture and horticulture, they have not been put into practical use due to their not satisfactorily high activities and their phytotoxicities. On the other hand, serious diseases of fruit trees, vegetables or cereals such as mildew, blight, powdery mildew and rust have hitherto been treated with various chemicals, all of which are unusable or of restricted use due to resistance to the chemicals. Therefore, development of novel fungicides different in skelton structure from prior-art chemicals has become a big problem in these fields.

DETAILED DESCRIPTION OF THE INVENTION

To attain the above-mentioned object, we have synthesized a large number of compounds and studied their usefulness. As a result, we were successful in the synthesis of the guanidine derivatives of the below-mentioned formula (I), and found that these derivatives are new compounds not disclosed in any literature and furthermore they have higher fugicidal activity and safety for agriculture and horticulture.

Therefore, the first aspect of the invention is guanidine derivatives represented by the formula

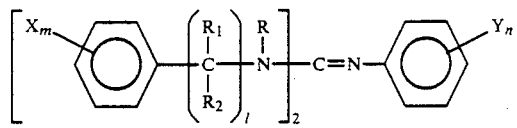

wherein R represents a hydrogen atom, a $(C_1-C_{10})$-alkyl group, a lower alkenyl group, a lower alkynyl group, a $(C_5-C_6)$-cycloalkyl-lower alkyl group or a $(C_5-C_7)$-cycloalkyl group which may be substituted with a lower alkyl group, X represents a hydrogen atom, a halogen atom, a lower alkyl group, a lower alkoxy group, a lower haloalkyl group or a lower haloalkoxy group, Y represents a hydrogen atom, a halogen atom, a lower alkyl group or a lower alkoxy group, $R_1$ and $R_2$ independently represent a hydrogen atom or a methyl group, and l, m and n independently represent an integer of 1 or 2 except that R, X, Y, $R_1$ and $R_2$ each are a hydrogen atom and l is 1.

The lower alkyl group as used herein means an alkyl group having 1-6 carbon atoms such as methyl, ethyl, propyl, isopropyl, butyl, isobutyl, sec-butyl, t-butyl, pentyl or hexyl.

When R is a lower alkenyl group, it is an alkenyl group having 2-6 carbon atoms such as vinyl, allyl, 1-propen-2-yl, butenyl, pentenyl or hexenyl.

When R is a lower alkynyl group, it is an alkynyl group having 2-4 carbon atoms such as ethynyl, propargyl, 1-propyn-2-yl or butynyl.

When X and Y independently are a lower alkoxy group, they are an alkoxy group having 1-5 carbon atoms such as methoxy, ethoxy, propoxy, isopropoxy, butoxy or pentyloxy.

Examples of a cycloalkyl-lower alkyl group for R include cyclopentylmethyl, cyclopentylethyl, cyclohexylmethyl and cyclohexylethyl.

Examples of a $(C_5-C_7)$-cycloalkyl group optionally substituted with a lower alkyl group include cyclopentyl, cyclohexyl, cycloheptyl which are optionally substituted with methyl, ethyl, n-propyl, iso-propyl or n-butyl.

The second aspect of the invention is a fungicide for agriculture and horticulture containing as an active ingredient a dibenzylguanidine derivative of the above-mentioned formula (I).

Examples of the inventive compounds of the formula (I) are shown in Table 1.

It is to be noted that the compound Nos. will be referred to also in Examples and Test Examples below.

TABLE 1

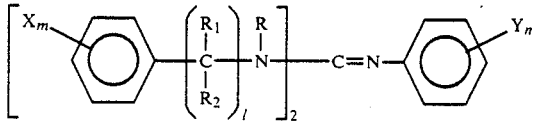

(I)

| Compound No. | R | $X_m$ | $Y_n$ | $\left(\begin{array}{c}R_1\\ -C-\\ R_2\end{array}\right)_l$ | Physical data |
|---|---|---|---|---|---|
| 1 | H— | 4-Cl | H | $CH_2$ | $n_D^{23}$ 1.6259 |
| 2 | H— | 4-$CH_3$— | H | $CH_2$ | $n_D^{23}$ 1.6112 |
| 3 | H— | 2-$CH_3$O— | H | $CH_2$ | $n_D^{23}$ 1.6308 |
| 4 | $CH_3$— | H— | H | $CH_2$ | $n_D^{23}$ 1.6071 |
| 5 | $CH_3$— | 2-Cl— | H | $CH_2$ | m.p. 81–84° C. |
| 6 | $CH_3$— | 4-Cl— | H | $CH_2$ | $n_D^{23}$ 1.6042 |
| 7 | $CH_3$— | 4-$CH_3$— | H | $CH_2$ | $n_D^{23}$ 1.5985 |
| 8 | $CH_3$— | 4-$CF_3$— | H | $CH_2$ | $n_D^{23}$ 1.5994 |
| 9 | $C_2H_5$— | H— | H | $CH_2$ | $n_D^{23}$ 1.5966 |
| 10 | $C_2H_5$— | 4-Cl | H | $CH_2$ | m.p. 73–75° C. |
| 11 | n-$C_3H_7$— | H— | H | $CH_2$ | $n_D^{23}$ 1.5831 |
| 12 | n-$C_3H_7$— | 3-Cl | H | $CH_2$ | $n_D^{23}$ 1.5884 |
| 13 | iso-$C_3H_7$— | H— | H | $CH_2$ | $n_D^{23}$ 1.5847 |
| 14 | iso-$C_3H_7$— | 4-Cl— | H | $CH_2$ | m.p. 122–125° C. |
| 15 | iso-$C_3H_7$— | 4-tert-$C_4H_9$— | H | $CH_2$ | m.p. 96–97° C. |
| 16 | n-$C_4H_9$— | 2-$CH_3$— | H | $CH_2$ | $n_D^{23}$ 1.6005 |
| 17 | cyclopentyl-H | H— | H | $CH_2$ | m.p. 106–107° C. |
| 18 | cyclopentyl-H | 2-Cl— | H | $CH_2$ | m.p. 108–111° C. |
| 19 | cyclopentyl-H | 4-Cl— | H | $CH_2$ | m.p. 140–141° C. |
| 20 | cyclopentyl-H | 2-$CH_3$— | H | $CH_2$ | $n_D^{23}$ 1.6049 |
| 21 | cyclopentyl-H | 4-$CHF_2$O— | H | $CH_2$ | m.p. 86.5–88° C. |
| 22 | cyclohexyl-H | H— | H | $CH_2$ | m.p. 164–166° C. |
| 23 | cyclohexyl-H | 4-Cl— | H | $CH_2$ | m.p. 174–175° C. |
| 24 | cyclohexyl-H | 3-iso-$C_3H_7$O— | H | $CH_2$ | $n_D^{23}$ 1.5946 |

TABLE 1-continued $$[X_m-\text{Ph}-(\underset{R_2}{\overset{R_1}{C}})_l-\underset{}{\overset{R}{N}}]_2-C=N-\text{Ph}-Y_n \qquad (I)$$

| Compound No. | R | $X_m$ | $Y_n$ | $(\underset{R_2}{\overset{R_1}{C}})_l$ | Physical data |
|---|---|---|---|---|---|
| 25 | cyclohexyl-H | 4-CHF$_2$O— | H | CH$_2$ | m.p. 118–120° C. |
| 26 | CH$_3$— | 4-F— | H | CH$_2$ | $n_D^{23}$ 1.6130 |
| 27 | CH$_3$— | 3-Cl— | H | CH$_2$ | $n_D^{23}$ 1.5842 |
| 28 | CH$_3$— | 4-CH$_3$O— | H | CH$_2$ | $n_D^{23}$ 1.5555 |
| 29 | iso-C$_3$H$_7$— | 2-Cl— | H | CH$_2$ | $n_D^{23}$ 1.5470 |
| 30 | iso-C$_3$H$_7$— | 3-Cl— | H | CH$_2$ | $n_D^{23}$ 1.5571 |
| 31 | iso-C$_3$H$_7$— | 4-CH$_3$O— | H | CH$_2$ | m.p. 145–146° C. |
| 32 | n-C$_4$H$_9$— | 2-Cl— | H | CH$_2$ | $n_D^{23}$ 1.5269 |
| 33 | sec-C$_4$H$_9$— | 4-Cl— | H | CH$_2$ | m.p. 120–122° C. |
| 34 | cyclopentyl-H | 2-F— | H | CH$_2$ | m.p. 126–127° C. |
| 35 | cyclopentyl-H | 3-Cl— | H | CH$_2$ | m.p. 90–92° C. |
| 36 | cyclopentyl-H | 4-Br— | H | CH$_2$ | m.p. 159–160° C. |
| 37 | cyclopentyl-H | 4-CH$_3$— | H | CH$_2$ | m.p. 118–119° C. |
| 38 | cyclopentyl-H | 4-tert-C$_4$H$_9$— | H | CH$_2$ | m.p. 105–108° C. |
| 39 | cyclopentyl-H | 4-CH$_3$O— | H | CH$_2$ | m.p. 143.5–144.5° C. |
| 40 | cyclohexyl-H | 4-F— | H | CH$_2$ | m.p. 183–184° C. |
| 41 | cyclohexyl-H | 2-Cl— | H | CH$_2$ | m.p. 147–148° C. |
| 42 | cyclohexyl-H | 3-Cl— | H | CH$_2$ | m.p. 135–136° C. |

TABLE 1-continued

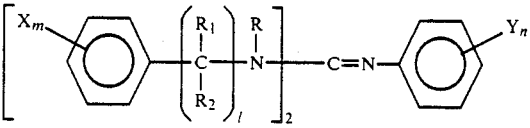

| Compound No. | R | $X_m$ | $Y_n$ | $\left(\begin{array}{c}R_1\\|\\C\\|\\R_2\end{array}\right)_l$ | Physical data |
|---|---|---|---|---|---|
| 43 | 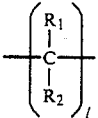 | 4-Br— | H | $CH_2$ | m.p. 164–172° C. |
| 44 | 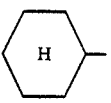 | 2-$CH_3$— | H | $CH_2$ | m.p. 72–75° C. |
| 45 | 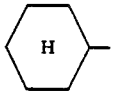 | 3-$CH_3$— | H | $CH_2$ | m.p. 128–129° C. |
| 46 | 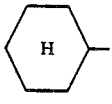 | 4-$CH_3$— | H | $CH_2$ | m.p. 172–173° C. |
| 47 | 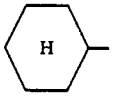 | 4-tert-$C_4H_9$— | H | $CH_2$ | m.p. 136–138° C. |
| 48 | 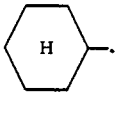 | 4-$CH_3O$— | H | $CH_2$ | m.p. 123–124° C. |
| 49 | H— | 2-Cl— | 4-$CH_3$— | $CH_2$ | $n_D^{23}$ 1.6122 |
| 50 | H— | 3-Cl— | 4-$CH_3$— | $CH_2$ | $n_D^{23}$ 1.6039 |
| 51 | H— | 4-Cl— | 4-$CH_3$— | $CH_2$ | $n_D^{23}$ 1.6048 |
| 52 | $CH_3$— | 4-Cl— | 4-F— | $CH_2$ | $n_D^{23}$ 1.5867 |
| 53 | $CH_3$— | 4-Cl— | 4-Cl— | $CH_2$ | $n_D^{23}$ 1.5354 |
| 54 | $CH_3$— | 4-Cl— | 4-$CH_3$— | $CH_2$ | $n_D^{23}$ 1.5258 |
| 55 | $CH_3$— | 4-Cl— | 4-$CH_3$— | $CH_2$ | $n_D^{23}$ 1.5786 |
| 56 | $CH_3$— | 4-Cl— | 2,6-$(CH_3)_2$— | $CH_2$ | $n_D^{23}$ 1.5603 |
| 57 | $CH_3$— | 4-$CF_3$— | 3-Cl— | $CH_2$ | $n_D^{23}$ 1.5876 |
| 58 | $CH_3$— | 3-iso-$C_3H_7$— | 2-$CH_3$— | $CH_2$ | $n_D^{23}$ 1.5334 |
| 59 | $C_2H_5$— | 3-Cl— | 2-$CH_3$— | $CH_2$ | $n_D^{23}$ 1.5842 |
| 60 | $C_2H_5$— | 4-Cl— | 2,6-$(CH_3)_2$— | $CH_2$ | $n_D^{23}$ 1.5729 |
| 61 | $C_2H_5$— | 2-$CH_3$— | 2-Cl— | $CH_2$ | $n_D^{23}$ 1.5858 |
| 62 | n-$C_3H_7$— | 2-Cl— | 3-$CH_3$— | $CH_2$ | $n_D^{23}$ 1.5702 |
| 63 | n-$C_3H_7$— | 4-$CH_3$— | 3-Cl— | $CH_2$ | $n_D^{23}$ 1.5619 |
| 64 | iso-$C_3H_7$— | 2-Cl— | 2,4-$Cl_2$— | $CH_2$ | $n_D^{23}$ 1.5375 |
| 65 | iso-$C_3H_7$— | 4-Cl— | 4-$CH_3O$— | $CH_2$ | $n_D^{23}$ 1.5778 |
| 66 | iso-$C_3H_7$— | 4-Cl— | 2,6-$(CH_3)_2$— | $CH_2$ | m.p. 107–110° C. |
| 67 | iso-$C_3H_7$— | 4-$CF_3$— | 4-Cl— | $CH_2$ | $n_D^{23}$ 1.5444 |
| 68 | n-$C_4H_9$— | 4-Cl— | 3-$CH_3$— | $CH_2$ | $n_D^{23}$ 1.5287 |
| 69 | 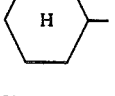 | 2-$CH_3$— | 3-iso-$C_3H_7O$— | $CH_2$ | $n_D^{23}$ 1.5763 |

TABLE 1-continued $$\left[X_m-\underset{}{\underset{}{\bigcirc}}-\left(\underset{R_2}{\overset{R_1}{\underset{|}{C}}}\right)_l\right]_2 \overset{R}{\underset{|}{N}}-C=N-\underset{}{\underset{}{\bigcirc}}-Y_n \quad (I)$$

| Compound No. | R | $X_m$ | $Y_n$ | $\left(\underset{R_2}{\overset{R_1}{\underset{|}{C}}}\right)_l$ | Physical data |
|---|---|---|---|---|---|
| 70 | cyclopentyl-H | 3-CH$_3$— | 2-CH$_3$— | CH$_2$ | $n_D^{23}$ 1.5311 |
| 71 | cyclopentyl-H | 4-tert-C$_4$H$_9$— | 2-Cl— | CH$_2$ | $n_D^{23}$ 1.5367 |
| 72 | cyclopentyl-H | 2-CH$_3$— | 4-Cl— | CH$_2$ | $n_D^{23}$ 1.5803 |
| 73 | cyclopentyl-H | 4-CHF$_2$O— | 4-CH$_3$— | CH$_2$ | $n_D^{23}$ 1.5226 |
| 74 | cyclohexyl-H | H— | 4-F— | CH$_2$ | m.p. 173–175° C. |
| 75 | cyclohexyl-H | H— | 4-Cl— | CH$_2$ | m.p. 145–147° C. |
| 76 | cyclohexyl-H | H— | 4-CH$_3$— | CH$_2$ | m.p. 128–130° C. |
| 77 | cyclohexyl-H | H— | 4-CH$_3$O— | CH$_2$ | m.p. 168–170° C. |
| 78 | cyclohexyl-H | 4-Cl— | 4-F— | CH$_2$ | m.p. 179–181° C. |
| 79 | cyclohexyl-H | 4-Cl— | 4-Cl— | CH$_2$ | m.p. 172–174° C. |
| 80 | cyclohexyl-H | 4-Cl— | 4-CH$_3$— | CH$_2$ | m.p. 135–137° C. |

TABLE 1-continued

| Compound No. | R | $X_m$ | $Y_n$ | $\left(\begin{array}{c}R_1\\C\\R_2\end{array}\right)_l$ | Physical data |
|---|---|---|---|---|---|
| 81 | cyclohexyl | 4-Cl— | 4-CH$_3$O— | CH$_2$ | m.p. 187–189.5° C. |
| 82 | cyclohexyl | 4-Cl— | 2,6-(CH$_3$)$_2$— | CH$_2$ | m.p. 168–170° C. |
| 83 | cyclohexyl | 4-CF$_3$— | 3-iso-C$_3$H$_7$O— | CH$_2$ | $n_D^{23}$ 1.5952 |
| 84 | H— | 2,4-Cl$_2$— | H | CH$_2$ | m.p. 61–63° C. |
| 85 | CH$_3$ | 2,4-Cl$_2$— | H | CH$_2$ | $n_D^{23}$ 1.5749 |
| 86 | iso-C$_3$H$_7$ | 2,4-Cl$_2$— | H | CH$_2$ | m.p. 163–166° C. |
| 87 | cyclopentyl | 2,4-Cl$_2$— | H | CH$_2$ | m.p. 121–123° C. |
| 88 | cyclohexyl | 2,4-Cl$_2$— | H | CH$_2$ | m.p. 175–176° C. |
| 89 | n-C$_{10}$H$_{21}$— | 4-Cl— | H | CH$_2$ | $n_D^{23}$ 1.4914 |
| 90 | CH$_2$=CHCH$_2$— | 4-Cl— | H | CH$_2$ | $n_D^{23}$ 1.5466 |
| 91 | CH≡CCH$_2$— | 4-Cl— | H | CH$_2$ | $n_D^{23}$ 1.5526 |
| 92 | CH$_3$CH=CHCH$_2$— | 4-Cl— | H | CH$_2$ | $n_D^{23}$ 1.5497 |
| 93 | 2-methylcyclohexyl | 4-Cl— | H | CH$_2$ | m.p. 118–131° C. |
| 94 | 3-methylcyclohexyl | 4-Cl— | H | CH$_2$ | m.p. 98–100° C. |
| 95 | 4-methylcyclohexyl | 4-Cl— | H | CH$_2$ | m.p. 193–196° C. |
| 96 | cycloheptyl | 4-Cl— | H | CH$_2$ | m.p. 162–164° C. |

TABLE 1-continued $$\left[X_m-\underset{}{\bigcirc}-\left(\underset{R_2}{\overset{R_1}{\underset{|}{C}}}\right)_l\right]_2 \overset{R}{\underset{|}{N}}-C=N-\underset{}{\bigcirc}-Y_n \quad (I)$$

| Compound No. | R | $X_m$ | $Y_n$ | $\left(\underset{R_2}{\overset{R_1}{\underset{|}{C}}}\right)_l$ | Physical data |
|---|---|---|---|---|---|
| 97 | ⌷—CH₂— (cyclopentyl) | 4-Cl— | H | CH₂ | $n_D^{23}$ 1.5672 |
| 98 | ⌬—CH₂— (cyclohexyl) | 4-Cl— | H | CH₂ | m.p. 131–132° C. |
| 99 | H— | H— | H | —CH(CH₃)— | $n_D^{23}$ 1.5022 |
| 100 | H— | H— | H | —C(CH₃)₂— | $n_D^{23}$ 1.4983 |
| 101 | H— | H— | H | —CH₂CH₂— | $n_D^{23}$ 1.5255 |
| 102 | ⌬— (cyclohexyl) | H— | H | —CH₂CH₂— | m.p. 108–109° C. |
| 103 | ⌬— (cyclohexyl) | 4-Cl— | H | —CH₂CH₂— | $n_D^{23}$ 1.4924 |

The present compounds of the formula (I) are novel compounds which are effective as an active ingredient in fungicides for agriculture and horticulture.

Process for preparing the present compounds the compounds of the formula (I) according to the invention can be prepared by the procedures as described below. The compounds can be prepared by reacting a phenylisocyanide dichloride represented by the formula (II) with a benzylamine derivative represented by the formula (III).

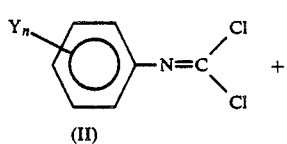

(II)

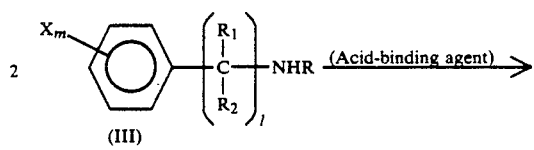

(III)

-continued

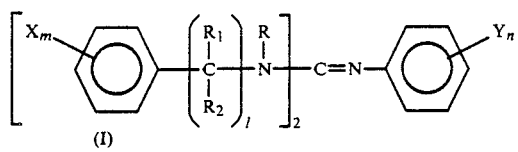

(I)

wherein R, X, Y, $R_1$, $R_2$, l, m and n have the same meanings as defined above.

The condensation reaction is usually carried out in an organic solvent. The solvent that may be employed includes hydrocarbons such as toluene and hexane, halogenated hydrocarbons such as chloroform and chlorobenzene, ethers such as ethyl ether, dioxane and tetrahydrofuran, nitriles such as acetonitrile and propionitrile, alcohols such as methanol and ethanol and dimethylsulfoxide.

As the compounds of the formula (III) are basic substances, they may be used in excess in place of the acid-binding agent. Alternatively, inorganic bases such as sodium hydride, sodium amide, sodium hydroxide and potassium carbonate, and organic bases such as triethylamine and pyridine may be used as the acid-binding agent.

Whereas the reaction proceeds at room temperature, heating at a temperature up to boiling point of the solvent used can shorten the reaction time. After completion of the reaction, salts of the acid-binding agent, if any, are separated by filtration, and the desired product can be obtained by removing the solvent by distillation. Alternatively, the desired product can be separated by the addition of water and an organic solvent such as benzene, toluene, tetrahydrofuran or chloroform. The compound of the invention is obtained by removal of the solvent by distillation.

The starting compounds (II) and (III) are known compounds. Examples 1-4 specifically illustrate the preparation according to the above procedures.

Preparative Example 1

Preparation of
1,3-dibenzyl-1,3-diisopropyl-2-phenylguanidine
(Compound No. 13)

In a 500-ml four-necked flask were placed 59.6 g of N-isopropylbenzylamine and 200 ml of acetonitrile. After cooling with water 17.4 g of phenylisocyanide dichloride was added dropwise. The mixture was then stirred at 50° C. for 3 hours. After cooling, precipitated salts were separated by filtration, the filtrate concentrated and finally water and toluene added to the residue. The toluene layer was washed with an aqueous 1N-hydrochloric acid and concentrated under reduced pressure to afford 36.7 g of the title compound as a pale yellow oil. The oil was purified by column chromotography on silica gel using a hexane-acetone mixture to give a colorless oil (yield 24.5 g), $n_D^{23}=1.5847$.

Preparative Example 2

Preparation of
1,3-dicyclopentyl-1,3-di(4-difluoromethoxybenzyl)-2phenylguanidine (Compound No. 21)

In a 500-ml four-necked flask were placed 48.2 g of N-cyclopentyl-4-difluoromethoxybenzylamine, 20.2 g of triethylamine and 200 ml of dioxane. Under cooling with water 17.4 g of phenylisocyanide dichloride was added dropwise followed by stirring under reflux for 2 hours. After cooling the reaction mixture was treated in the same way as in Example 1 to afford 53.6 g of the title compound as pale brown crystals. The product was recrystallized from a hexane-ethyl acetate mixture to give white crystals (yield 28.2 g), m.p. 86.5°–88° C.

Preparative Example 3

Preparation of
1,3-dimethyl-1,3-di(4-chlorobenzyl)-2-(2,6-dimethylphenyl) guanidine (Compound No. 56)

In a 500-ml four-necked flask were placed 31.1 g of N-methyl-4-chlorobenzylamine and 200 ml of acetonitrile. After cooling with water 20.2 g of 2,6-dimethylphenylisocyanide dichloride was added dropwise followed by stirring at 50° C. for 3 hours. After cooling the reaction mixture was treated in the same way as in Example 1 to afford 37.4 g of the title compound as a pale yellow oil. The product was purified by column chromatography on silica gel using a hexane-acetone mixture to give a colorless oil (yield 30.3 g), $n_D^{23}=1.5603$ Preparative Example 4

Preparation of
1,3-dicyclohexyl-1,3-dibenzyl-2-(4-methylphenyl)-guanidine (Compound No. 76)

In a 500-ml four-necked flask were placed 37.8 g of N-cyclohexylbenzylamine, 20.2 g of triethylamine and 200 ml of dioxane. Under cooling with water 18.8 g of 4-methylphenylisocyanide dichloride was added dropwise followed by stirring under reflux for 2 hours. After cooling, the reaction mixture was treated in the same way as in Example 1 to afford 25.6 g of the title compound as pale brown crystals. The product was recrystallized from a hexane-ethyl acetate mixture to give white crystals (yield 13.4 g), m.p. 128°–130° C.

Method for formulating fungicides for agriculture and horticulture

The agricultural and horticultural fungicides of the invention can be prepared by formulating the compounds of the above-mentioned formula (I) in a conventional form. Thus, the compounds of the formula (I) may be compounded with suitable carriers and adjuvants, e.g., surface active agents, binders, stabilizers or the like to formulate wettable powder, emulsifiable concentrate, liquid formulation, sol (flowable formulation), oil solution, dust, DL (Driftless type) dust, microgranules, coarse dust or the like. The content (%) of the present compound in these formulations may range from 1 to 90% by weight for wettable powder, emulsifiable concentrate, liquid formulation, sol and oil solution, from 0.5 to 10% by weight for dust, DL dust, microgranules and coarse dust.

The method for using the agricultural and horticultural fungicides of the invention is illustrated below. In the application of wettable powder, liquid formulation, emulsifiable concentrate, sol (flowable formulation) and oil solution, they are diluted to 500-2000 times with water and generally adjusted to a solution containing 1 to 10000 ppm of the active ingredient. This diluted solution is sprayed over the foliage in the disease infection area of plant in an amount of 50 to 300 liters, usually 100 to 200 liters per 10 ares.

The liquid formulation, emulsifiable concentrate and sol (flowable formulation) are sprayed as a concentrated solution without dilution with water or a solution diluted to 10 times or less with water, principally as ultra low volume spray (LV spray, ULV spray) for aerial application in an amount of about 50 to 3000 ml per 10 ares using helicopter or the like.

The dust, DL dust, microgranules and coarse dust are applied to the foliage in the disease infection area of plant, in soil and onto the surface of soil or water, in an amount of to 5 kg per 10 ares (about 50 to 500 g as active ingredient).

The method for formulating the inventive compounds of the general formula (I) into agricultural and horticultural fungicides will be illustrated below in Examples 5-8.

Example 5

Dust

A homogeneous mixture of 2 parts of Compound No. 13, 1 part of PAP (Modifier of physical properties) and 97 parts of clay was pulverized to obtain a dust containing 0.2% of the active ingredient.

Example 6

Wettable powder

A homogeneous mixture of 20 parts of Compound No. 21, 3 parts of potassium alkylbenzenesulfonate, 5 parts of polyoxyethylene nonyl phenyl ether and 72 parts of clay was pulverized to give a wettable powder containing 20% of the active ingredient.

Example 7

Emulsifiable concentrate 30 parts of Compound No. 3, 40 parts of methyl ethyl ketone and 30 parts of polyoxyethylene nonyl phenyl ether were mixed and dissolved to give an emulsifiable concentrate containing 30% of the active ingredient.

Example 8

Sol 40 parts of Compound No. 25, 2 parts of lauryl sulfate, 2 parts of sodium alkylnaphthalenesulfonate, 1 part of acetoxypropyl cellulose and 55 parts of water were blended homogeneously to give a sol containing 40% of the active ingredient.

The novel compounds of the invention possess high control effects on mildew, blight, powdery mildew and rust which are serious diseases of fruit trees, vegetables or cereals, and are useful as agricultural and horticultural fungicides.

Usefulness and embodiments of the inventive compounds of the formula (I) will be shown with reference to Test Example 1–4.

Test Example 1

Test for the control effect on cucumber downy mildew

The second-leaf stage young seedlings of cucumber (variety: Sagami hanjiro) soil-cultured in a pot of 9 cm in diameter in a greenhouse was applied 20 ml per pot of a test liquid which was prepared by diluting a wettable powder prepared according to Example 6 to a predetermined concentration. One day after the application, the seedling was inoculated by spraying with a spore suspension of cucumber downy mildew fungus (*Pseudoperonospora cubensis*) which had been prepared by scraping spores with a wet brush off a fungus-infected leaf, suspending the spores in a 50 ppm aqueous solution of sticker (polyoxyethylene alkyl ether) and adjusting the suspension to a concentration of $5 \times 10^6$ spores/ml. The seedlings were allowed to stand for 2 days at 20° C. and 100% humidity to induce the disease development. Six days after the inoculation, the area (%) of lesions per leaf was observed, and the control value (%) was calculated according to the equation shown below.

The test was conducted in two-series of pots for each concentration of the test liquid, and an average control value (%) was calculated to make an evaluation on the basis of the index given below. Furthermore, the phytotoxicity against cucumber was assessed. The results are shown in Table 2.

It is to be noted that the same evaluation of the fungicidal effect and the same examination of the phytotoxicity score as in this example were run also in Test Examples 2–4.

$$\text{Control value (\%)} = \left(1 - \frac{\text{Area of lesions per leaf in treated pot}}{\text{Area of lesions per leaf in untreated pot}}\right) \times 100$$

| Index of fungicidal effect | Control value |
|---|---|
| 5 | 100% |
| 4 | 80–<100% |
| 3 | 60–<80% |
| 2 | 40–<60% |
| 1 | 20–<40% |
| 0 | <20% |

Index of phytotoxicity
5: Very severe
4: Severe
3: Moderate
2: Some
1: Slight
0: No

TABLE 2

| Test compound No. | Concentration (ppm) | Index of the effect | Phytotoxicity |
|---|---|---|---|
| 1 | 100 | 4 | 0 |
| 2 | 100 | 4 | 0 |
| 3 | 100 | 5 | 0 |
| 4 | 100 | 4 | 0 |
| 5 | 100 | 5 | 0 |
| 6 | 100 | 5 | 0 |
| 7 | 100 | 5 | 0 |
| 8 | 100 | 5 | 0 |
| 9 | 100 | 4 | 0 |
| 10 | 100 | 5 | 0 |
| 11 | 100 | 4 | 0 |
| 12 | 100 | 5 | 0 |
| 13 | 100 | 4 | 0 |
| 14 | 100 | 5 | 0 |
| 15 | 100 | 5 | 0 |
| 16 | 100 | 5 | 0 |
| 17 | 100 | 4 | 0 |
| 18 | 100 | 5 | 0 |
| 19 | 100 | 5 | 0 |
| 20 | 100 | 5 | 0 |
| 21 | 100 | 5 | 0 |
| 22 | 100 | 4 | 0 |
| 23 | 100 | 5 | 0 |
| 24 | 100 | 5 | 0 |
| 25 | 100 | 5 | 0 |
| 26 | 100 | 5 | 0 |
| 27 | 100 | 5 | 0 |
| 28 | 100 | 4 | 0 |
| 29 | 100 | 5 | 0 |
| 30 | 100 | 5 | 0 |
| 31 | 100 | 4 | 0 |
| 32 | 100 | 5 | 0 |
| 33 | 100 | 4 | 0 |
| 34 | 100 | 5 | 0 |
| 35 | 100 | 5 | 0 |
| 36 | 100 | 5 | 0 |
| 37 | 100 | 5 | 0 |
| 38 | 100 | 5 | 0 |
| 39 | 100 | 5 | 0 |
| 40 | 100 | 5 | 0 |
| 41 | 100 | 5 | 0 |
| 42 | 100 | 5 | 0 |
| 43 | 100 | 5 | 0 |
| 44 | 100 | 5 | 0 |
| 45 | 100 | 5 | 0 |
| 46 | 100 | 5 | 0 |
| 47 | 100 | 5 | 0 |
| 48 | 100 | 5 | 0 |
| 49 | 100 | 4 | 0 |
| 50 | 100 | 4 | 0 |
| 51 | 100 | 4 | 0 |
| 52 | 100 | 4 | 0 |
| 53 | 100 | 5 | 0 |

TABLE 2-continued

| Test compound No. | Concentration (ppm) | Index of the effect | Phytotoxicity |
|---|---|---|---|
| 54 | 100 | 5 | 0 |
| 55 | 100 | 5 | 0 |
| 56 | 100 | 5 | 0 |
| 57 | 100 | 4 | 0 |
| 58 | 100 | 4 | 0 |
| 59 | 100 | 4 | 0 |
| 60 | 100 | 5 | 0 |
| 61 | 100 | 4 | 0 |
| 62 | 100 | 4 | 0 |
| 63 | 100 | 5 | 0 |
| 64 | 100 | 4 | 0 |
| 65 | 100 | 5 | 0 |
| 66 | 100 | 5 | 0 |
| 67 | 100 | 4 | 0 |
| 68 | 100 | 4 | 0 |
| 69 | 100 | 4 | 0 |
| 70 | 100 | 5 | 0 |
| 71 | 100 | 5 | 0 |
| 72 | 100 | 4 | 0 |
| 73 | 100 | 4 | 0 |
| 74 | 100 | 5 | 0 |
| 75 | 100 | 5 | 0 |
| 76 | 100 | 5 | 0 |
| 77 | 100 | 5 | 0 |
| 78 | 100 | 5 | 0 |
| 79 | 100 | 4 | 0 |
| 80 | 100 | 5 | 0 |
| 81 | 100 | 5 | 0 |
| 82 | 100 | 5 | 0 |
| 83 | 100 | 4 | 0 |
| 84 | 100 | 5 | 0 |
| 85 | 100 | 5 | 0 |
| 86 | 100 | 5 | 0 |
| 87 | 100 | 5 | 0 |
| 88 | 100 | 5 | 0 |
| 89 | 100 | 4 | 0 |
| 90 | 100 | 4 | 0 |
| 91 | 100 | 4 | 0 |
| 92 | 100 | 4 | 0 |
| 93 | 100 | 5 | 0 |
| 94 | 100 | 5 | 0 |
| 95 | 100 | 5 | 0 |
| 96 | 100 | 5 | 0 |
| 97 | 100 | 4 | 0 |
| 98 | 100 | 5 | 0 |
| 99 | 100 | 4 | 0 |
| 100 | 100 | 5 | 0 |
| 101 | 100 | 5 | 0 |
| 102 | 100 | 4 | 0 |
| 103 | 100 | 5 | 0 |
| Comparative compound A | 100 | 2 | 3 |
| Comparative compound B | 100 | 4 | 1 |
| Untreated | — | 0 (93.6) | — |

(Note)
The parenthesized number in the untreated indicates percent of lesion area per leaf.
Comparative compound A:

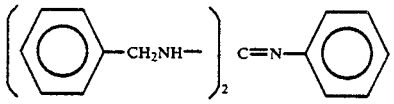

(Compound disclosed in Japanese Patent Publication No. 29742/1968 and No. 9846/1975)
(Comparative compound B:

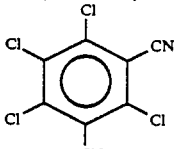

(Generic name: Chlorothalonil)

Test Example 2

Test for control effect on tomato late blight

The young seedlings of tomato (variety: Toko K, the fifth leaf stage seedlings) soil cultured in a vinyl pot of 9 cm in diameter in a greenhouse was applied by means of an auto-sprayer 60 ml per 3 pots of a test liquid. The test liquid had been prepared by diluting a wettable powder prepared according to the procedure of Example 6 to a predetermined concentration. On the next day after completion of the spraying of the test liquid, the leaves of treated seedlings were inoculated by spraying a zoosporangium suspension of pathogenic fungus (*Phytophthora infestans*) by a hand sprayer. The zoosporangia had been rinsed out of the fungus cultivated on potato tubers at 20° C. for 5 days, and the suspension prepared at a zoosporangim concentration of $10^5$/ml. The seedlings were then kept in a moist chamber at 20° C. and 100% humidity for 5 days followed by observation of the area (%) of lesions on the first to fourth leaves. Percent average area of lesions per leaf was calculated, and control value (%) determined in comparison with the untreated plot.

The test was conducted in two-series of pots for each concentration of the test liquid, and average control value (%) determined, which was translated into evaluation score.

Furthermore, the phytotoxicity against the tomato seedling of the test compound was investigated according to the same procedure as in Test Example 1. The results obtained are as shown in Table 3.

$$\text{Control value (\%)} = \left(1 - \frac{\text{\% of lesions per leaf in treated plot}}{\text{\% of lesions per leaf in untreated plot}}\right) \times 100$$

TABLE 3

| Test compound No. | Concentration (ppm) | Index of the effect | Phytotoxicity |
|---|---|---|---|
| 1 | 100 | 4 | 0 |
| 2 | 100 | 5 | 0 |
| 3 | 100 | 5 | 0 |
| 4 | 100 | 4 | 0 |
| 5 | 100 | 4 | 0 |
| 6 | 100 | 5 | 0 |
| 7 | 100 | 5 | 0 |
| 8 | 100 | 5 | 0 |
| 9 | 100 | 4 | 0 |
| 10 | 100 | 5 | 0 |
| 11 | 100 | 4 | 0 |
| 12 | 100 | 5 | 0 |
| 13 | 100 | 4 | 0 |
| 14 | 100 | 5 | 0 |
| 15 | 100 | 5 | 0 |
| 16 | 100 | 5 | 0 |
| 17 | 100 | 4 | 0 |
| 18 | 100 | 5 | 0 |
| 19 | 100 | 5 | 0 |
| 20 | 100 | 5 | 0 |
| 21 | 100 | 5 | 0 |
| 22 | 100 | 4 | 0 |
| 23 | 100 | 5 | 0 |
| 24 | 100 | 5 | 0 |
| 25 | 100 | 5 | 0 |
| 26 | 100 | 5 | 0 |
| 27 | 100 | 5 | 0 |
| 28 | 100 | 5 | 0 |
| 29 | 100 | 5 | 0 |
| 30 | 100 | 5 | 0 |
| 31 | 100 | 5 | 0 |
| 32 | 100 | 4 | 0 |
| 33 | 100 | 5 | 0 |
| 34 | 100 | 4 | 0 |
| 35 | 100 | 4 | 0 |
| 36 | 100 | 4 | 0 |
| 37 | 100 | 5 | 0 |

TABLE 3-continued

| Test compound No. | Concentration (ppm) | Index of the effect | Phyto-toxicity |
|---|---|---|---|
| 38 | 100 | 4 | 0 |
| 39 | 100 | 5 | 0 |
| 40 | 100 | 4 | 0 |
| 41 | 100 | 4 | 0 |
| 42 | 100 | 4 | 0 |
| 43 | 100 | 4 | 0 |
| 44 | 100 | 5 | 0 |
| 45 | 100 | 5 | 0 |
| 46 | 100 | 4 | 0 |
| 47 | 100 | 4 | 0 |
| 48 | 100 | 5 | 0 |
| 49 | 100 | 4 | 0 |
| 50 | 100 | 4 | 0 |
| 51 | 100 | 4 | 0 |
| 52 | 100 | 5 | 0 |
| 53 | 100 | 5 | 0 |
| 54 | 100 | 5 | 0 |
| 55 | 100 | 5 | 0 |
| 56 | 100 | 5 | 0 |
| 57 | 100 | 5 | 0 |
| 58 | 100 | 4 | 0 |
| 59 | 100 | 4 | 0 |
| 60 | 100 | 5 | 0 |
| 61 | 100 | 5 | 0 |
| 62 | 100 | 4 | 0 |
| 63 | 100 | 4 | 0 |
| 64 | 100 | 5 | 0 |
| 65 | 100 | 5 | 0 |
| 66 | 100 | 5 | 0 |
| 67 | 100 | 4 | 0 |
| 68 | 100 | 4 | 0 |
| 69 | 100 | 4 | 0 |
| 70 | 100 | 5 | 0 |
| 71 | 100 | 5 | 0 |
| 72 | 100 | 5 | 0 |
| 73 | 100 | 4 | 0 |
| 74 | 100 | 4 | 0 |
| 75 | 100 | 5 | 0 |
| 76 | 100 | 5 | 0 |
| 77 | 100 | 5 | 0 |
| 78 | 100 | 5 | 0 |
| 79 | 100 | 4 | 0 |
| 80 | 100 | 5 | 0 |
| 81 | 100 | 4 | 0 |
| 82 | 100 | 5 | 0 |
| 83 | 100 | 4 | 0 |
| 84 | 100 | 4 | 0 |
| 85 | 100 | 4 | 0 |
| 86 | 100 | 4 | 0 |
| 87 | 100 | 5 | 0 |
| 88 | 100 | 5 | 0 |
| 89 | 100 | 5 | 0 |
| 90 | 100 | 5 | 0 |
| 91 | 100 | 5 | 0 |
| 92 | 100 | 4 | 0 |
| 93 | 100 | 5 | 0 |
| 94 | 100 | 5 | 0 |
| 95 | 100 | 5 | 0 |
| 96 | 100 | 4 | 0 |
| 97 | 100 | 4 | 0 |
| 98 | 100 | 5 | 0 |
| 99 | 100 | 5 | 0 |
| 100 | 100 | 5 | 0 |
| 101 | 100 | 4 | 0 |
| 102 | 100 | 5 | 0 |
| 103 | 100 | 4 | 0 |
| Comparative compound | | | |
| A | 100 | 1 | 3 |
| B | 100 | 4 | 1 |
| Untreated | — | 0 (91.6) | — |

Note
1) The comparative compounds A and B are the same as those shown in Table 2.
2) The parenthesized figure in the untreated indicates the number of lesion per leaf.

Test Example 3

Test for the control effect on barley powdery mildew

Over the first-leaf stage seedlings of barley (variety: Azumagolden) soil-cultured in a biscuit pot of 9 cm in diameter in a greenhouse were sprayed 10 ml of a test liquid which had been prepared by diluting a wettable powder prepared according to Example 6 to a predetermined concentration. After allowing to stand overnight, the seedlings were inoculated by spraying with a spore suspension of powdery mildew fungus (*Erysiphe graminis*). Seven days after the inoculation, the number of lesion infected with barley powdery mildew was observed, and the control value (%) was calculated according to the formula below and translated into evaluation index. Furthermore, the phytotoxicity against the barley of the test compound was examined on the same ratings as described in Test Example 1. The results are shown in Table 4.

$$\text{Control value (\%)} = \left(1 - \frac{\text{Number of the lesion in treated pot}}{\text{Number of lesion in untreated pot}}\right) \times 100$$

TABLE 4

| Test compound. No. | Concentration (ppm) | Index of the effect | Phytotoxicity |
|---|---|---|---|
| 1 | 250 | 5 | 0 |
| 2 | 250 | 4 | 0 |
| 3 | 250 | 5 | 0 |
| 4 | 250 | 5 | 0 |
| 5 | 250 | 5 | 0 |
| 6 | 250 | 5 | 0 |
| 7 | 250 | 5 | 0 |
| 8 | 250 | 5 | 0 |
| 9 | 250 | 4 | 0 |
| 10 | 250 | 5 | 0 |
| 11 | 250 | 4 | 0 |
| 12 | 250 | 5 | 0 |
| 13 | 250 | 4 | 0 |
| 14 | 250 | 5 | 0 |
| 15 | 250 | 5 | 0 |
| 16 | 250 | 5 | 0 |
| 17 | 250 | 5 | 0 |
| 18 | 250 | 5 | 0 |
| 19 | 250 | 5 | 0 |
| 20 | 250 | 5 | 0 |
| 21 | 250 | 5 | 0 |
| 22 | 250 | 5 | 0 |
| 23 | 250 | 5 | 0 |
| 24 | 250 | 5 | 0 |
| 25 | 250 | 5 | 0 |
| 26 | 250 | 5 | 0 |
| 27 | 250 | 5 | 0 |
| 28 | 250 | 5 | 0 |
| 29 | 250 | 5 | 0 |
| 30 | 250 | 5 | 0 |
| 31 | 250 | 5 | 0 |
| 32 | 250 | 5 | 0 |
| 33 | 250 | 4 | 0 |
| 34 | 250 | 5 | 0 |
| 35 | 250 | 5 | 0 |
| 36 | 250 | 5 | 0 |
| 37 | 250 | 5 | 0 |
| 38 | 250 | 5 | 0 |
| 39 | 250 | 5 | 0 |
| 40 | 250 | 4 | 0 |
| 41 | 250 | 4 | 0 |
| 42 | 250 | 4 | 0 |
| 43 | 250 | 5 | 0 |
| 44 | 250 | 5 | 0 |
| 45 | 250 | 4 | 0 |
| 46 | 250 | 5 | 0 |
| 47 | 250 | 5 | 0 |

TABLE 4-continued

| Test compound No. | Concentration (ppm) | Index of the effect | Phytotoxicity |
|---|---|---|---|
| 48 | 250 | 4 | 0 |
| 49 | 250 | 4 | 0 |
| 50 | 250 | 4 | 0 |
| 51 | 250 | 4 | 0 |
| 52 | 250 | 4 | 0 |
| 52 | 250 | 5 | 0 |
| 53 | 250 | 5 | 0 |
| 54 | 250 | 5 | 0 |
| 55 | 250 | 5 | 0 |
| 56 | 250 | 5 | 0 |
| 57 | 240 | 4 | 0 |
| 58 | 250 | 4 | 0 |
| 59 | 250 | 4 | 0 |
| 60 | 250 | 5 | 0 |
| 61 | 250 | 4 | 0 |
| 62 | 250 | 4 | 0 |
| 63 | 250 | 5 | 0 |
| 64 | 250 | 5 | 0 |
| 65 | 250 | 5 | 0 |
| 66 | 250 | 5 | 0 |
| 67 | 250 | 5 | 0 |
| 68 | 250 | 5 | 0 |
| 69 | 250 | 4 | 0 |
| 70 | 250 | 4 | 0 |
| 71 | 250 | 4 | 0 |
| 72 | 250 | 4 | 0 |
| 73 | 250 | 4 | 0 |
| 74 | 250 | 4 | 0 |
| 75 | 250 | 5 | 0 |
| 76 | 250 | 5 | 0 |
| 77 | 250 | 5 | 0 |
| 78 | 250 | 5 | 0 |
| 79 | 250 | 5 | 0 |
| 80 | 250 | 4 | 0 |
| 81 | 250 | 5 | 0 |
| 82 | 250 | 4 | 0 |
| 83 | 250 | 4 | 0 |
| 84 | 250 | 5 | 0 |
| 85 | 250 | 5 | 0 |
| 86 | 250 | 5 | 0 |
| 87 | 250 | 5 | 0 |
| 88 | 250 | 5 | 0 |
| 89 | 250 | 4 | 0 |
| 90 | 250 | 5 | 0 |
| 91 | 250 | 4 | 0 |
| 92 | 250 | 4 | 0 |
| 93 | 250 | 5 | 0 |
| 94 | 250 | 5 | 0 |
| 95 | 250 | 5 | 0 |
| 96 | 250 | 5 | 0 |
| 97 | 250 | 4 | 0 |
| 98 | 250 | 5 | 0 |
| 99 | 250 | 4 | 0 |
| 100 | 250 | 4 | 0 |
| 101 | 250 | 5 | 0 |
| 102 | 250 | 5 | 0 |
| 103 | 250 | 5 | 0 |
| Comparative compound A | 250 | 2 | 2 |
| C | 250 | 4 | 1 |
| Untreated | — | 0 (50.6) | — |

Note
1) The comparative compound A is the same as the one shown in Table 2.
2) The parenthesized figure in the untreated indicates the number of the lesion per leaf.

Comparative compound C:

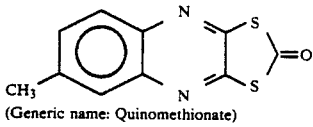

(Generic name: Quinomethionate)

Test Example 4

Test for the control effect on wheat leaf rust

Over the 1st-leaf stage young seedlings of wheat (variety: Norin No. 61) soil-cultured in a biscuit pot of 9 cm in diameter in a greenhouse was sprayed 20 ml per 3 pots of a test liquid which had been prepared by diluting a wettable powder prepared according to Example 6 to a predetermined concentration. One day after the spraying of the test liquid, the leaves to be treated were inoculated by spraying with a spore suspension of leaf rust fungus. The spore suspension had been prepared by suspending uredospores of wheat leaf rust fungus (*Puccinia recondita*) formed on the leaf of wheat in a distilled water containing 50 ppm of Tween 20 ® (trade name of polyoxyethylene sorbitan monolaurate, Kao Soap Co., Ltd.) so as to give about 50 spores as observed at one view under a microscope (×150). After keeping overnight in a moist chamber at 20° C., the treated seedlings were transferred to a disease development greenhouse at 20° C. to induce an incidence. Ten days after the inoculation, the seedlings were taken from the greenhouse and the number of uredosporus per leaf was counted and the control value (%) was calculated on the basis of the following formula. The test was performed in three-series of pots for each concentration of test compound to determine an average control value (%) which was translated into the evaluation index. Furthermore, the phytotoxicity against wheat of the test compound was examined on the same ratings as described in Test Example 1. The results are shown in Table 5.

$$\text{Control value (\%)} = \left(1 - \frac{\text{Number of uredosporus per treated leaf}}{\text{Number of uredosporus per untreated leaf}}\right) \times 100$$

TABLE 5

| Test compound No. | Concentration (ppm) | Index of the effect | Phytotoxicity |
|---|---|---|---|
| 1 | 250 | 4 | 0 |
| 2 | 250 | 5 | 0 |
| 3 | 250 | 5 | 0 |
| 4 | 250 | 4 | 0 |
| 5 | 250 | 5 | 0 |
| 6 | 250 | 5 | 0 |
| 7 | 250 | 5 | 0 |
| 8 | 250 | 5 | 0 |
| 9 | 250 | 5 | 0 |
| 10 | 250 | 5 | 0 |
| 11 | 250 | 4 | 0 |
| 12 | 250 | 5 | 0 |
| 13 | 250 | 4 | 0 |
| 14 | 250 | 5 | 0 |
| 15 | 250 | 5 | 0 |
| 16 | 250 | 5 | 0 |
| 17 | 250 | 4 | 0 |
| 18 | 250 | 5 | 0 |
| 19 | 250 | 5 | 0 |
| 20 | 250 | 5 | 0 |
| 21 | 250 | 5 | 0 |
| 22 | 250 | 4 | 0 |
| 23 | 250 | 5 | 0 |
| 24 | 250 | 5 | 0 |
| 26 | 250 | 5 | 0 |
| 27 | 250 | 5 | 0 |
| 28 | 250 | 5 | 0 |
| 29 | 250 | 5 | 0 |
| 30 | 250 | 5 | 0 |
| 31 | 250 | 5 | 0 |
| 32 | 250 | 5 | 0 |
| 33 | 250 | 4 | 0 |
| 34 | 250 | 5 | 0 |
| 35 | 250 | 5 | 0 |
| 36 | 250 | 4 | 0 |
| 37 | 250 | 5 | 0 |
| 38 | 250 | 5 | 0 |
| 39 | 250 | 5 | 0 |
| 40 | 250 | 4 | 0 |

TABLE 5-continued

| Test compound No. | Concentration (ppm) | Index of the effect | Phytotoxicity |
|---|---|---|---|
| 41 | 250 | 5 | 0 |
| 42 | 250 | 4 | 0 |
| 43 | 250 | 4 | 0 |
| 44 | 250 | 5 | 0 |
| 45 | 250 | 5 | 0 |
| 46 | 250 | 5 | 0 |
| 47 | 250 | 5 | 0 |
| 48 | 250 | 5 | 0 |
| 49 | 250 | 4 | 0 |
| 50 | 250 | 4 | 0 |
| 51 | 250 | 4 | 0 |
| 52 | 250 | 5 | 0 |
| 53 | 250 | 5 | 0 |
| 54 | 250 | 5 | 0 |
| 55 | 250 | 5 | 0 |
| 56 | 250 | 5 | 0 |
| 57 | 250 | 5 | 0 |
| 58 | 250 | 5 | 0 |
| 59 | 250 | 4 | 0 |
| 60 | 250 | 5 | 0 |
| 61 | 250 | 4 | 0 |
| 62 | 250 | 5 | 0 |
| 63 | 250 | 5 | 0 |
| 64 | 250 | 4 | 0 |
| 65 | 250 | 5 | 0 |
| 66 | 250 | 5 | 0 |
| 67 | 250 | 4 | 0 |
| 68 | 250 | 4 | 0 |
| 69 | 250 | 5 | 0 |
| 70 | 250 | 5 | 0 |
| 71 | 250 | 4 | 0 |
| 72 | 250 | 4 | 0 |
| 73 | 250 | 5 | 0 |
| 74 | 250 | 4 | 0 |
| 75 | 250 | 4 | 0 |
| 76 | 250 | 5 | 0 |
| 77 | 250 | 5 | 0 |
| 78 | 250 | 4 | 0 |
| 79 | 250 | 4 | 0 |
| 80 | 250 | 5 | 0 |
| 81 | 250 | 4 | 0 |
| 82 | 250 | 5 | 0 |
| 83 | 250 | 4 | 0 |
| 84 | 250 | 5 | 0 |
| 85 | 250 | 5 | 0 |
| 86 | 250 | 4 | 0 |
| 87 | 250 | 5 | 0 |
| 88 | 250 | 5 | 0 |
| 89 | 250 | 4 | 0 |
| 90 | 250 | 5 | 0 |
| 91 | 250 | 4 | 0 |
| 92 | 250 | 4 | 0 |
| 93 | 250 | 5 | 0 |
| 94 | 250 | 4 | 0 |
| 95 | 250 | 5 | 0 |
| 96 | 250 | 4 | 0 |
| 97 | 250 | 4 | 0 |
| 98 | 250 | 5 | 0 |
| 99 | 250 | 5 | 0 |
| 100 | 250 | 4 | 0 |
| 101 | 250 | 5 | 0 |
| 102 | 250 | 4 | 0 |
| 103 | 250 | 5 | 0 |
| Comparative A | 250 | 1 | 2 |
| compound D | 250 | 4 | 1 |
| untreated | — | 0 (49.2) | — |

Note
1) The comparative compound A is the same as that shown in Table 2.
2) The parenthesized number in the untreated indicates the number of the lesion per leaf.

Comparative compound D:

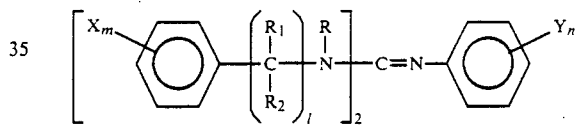

Zn (Generic name: Gineb)

What is claimed is:

1. A guanidine derivative represented by the formula

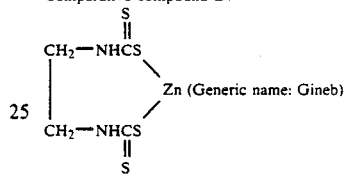

wherein R represents a ($C_5$–$C_6$)-cycloalkyl group, X represents a halogen atom, a lower alkyl group or a lower alkoxy group, Y represents a hydrogen atom, $R_1$ and $R_2$ represent a hydrogen atom, l, m and n represent an integer of 1.

2. A fungicidal composition for agriculture and horticulture containing as an active ingredient a dibenzylguanidine derivative of claim 1 and containing an inert carrier.

* * * * *